(12) United States Patent
Knox

(10) Patent No.: US 8,042,683 B2
(45) Date of Patent: Oct. 25, 2011

(54) CONTACT LENS SAFETY APPARATUS

(76) Inventor: Alastair Knox, Paisley (GB)

( * ) Notice: Subject to any disclaimer, the term of this patent is extended or adjusted under 35 U.S.C. 154(b) by 69 days.

(21) Appl. No.: 12/312,130

(22) PCT Filed: Jan. 11, 2007

(86) PCT No.: PCT/GB2007/004173
§ 371 (c)(1),
(2), (4) Date: Apr. 27, 2009

(87) PCT Pub. No.: WO2008/053220
PCT Pub. Date: May 8, 2008

(65) Prior Publication Data
US 2010/0044247 A1 Feb. 25, 2010

(30) Foreign Application Priority Data
Nov. 3, 2006 (GB) .................................. 0621903.4

(51) Int. Cl.
A45C 11/04 (2006.01)

(52) U.S. Cl. ........................... 206/5.1; 134/901; 294/1.2

(58) Field of Classification Search .................... 206/5.1; 134/901; D3/264; 294/1.2
See application file for complete search history.

(56) References Cited

U.S. PATENT DOCUMENTS

| 3,460,552 A | * | 8/1969 | Sturgeon | 206/5.1 |
| 3,643,672 A |   | 2/1972 | Brown |  |
| 3,822,780 A |   | 7/1974 | Allergan |  |
| 3,955,726 A |   | 5/1976 | Reitzel |  |
| 4,328,890 A |   | 5/1982 | Thomas et al. |  |
| 4,890,729 A |   | 1/1990 | Ranalletta |  |
| 4,942,959 A | * | 7/1990 | Sauber et al. | 206/5.1 |
| 6,244,430 B1 | * | 6/2001 | Travis | 206/5.1 |
| 2005/0087453 A1 |  | 4/2005 | Mahieu et al. |  |

* cited by examiner

Primary Examiner — J. Gregory Pickett

(57) ABSTRACT

A contact lens safety apparatus FIG. 1, invented as one unit with at least an elevating and de-elevating bowl (90). The contact lens safety apparatus can be opened or closed by lids (20) and a contact lens safely placed in (90), which can be sub-merged into solution (150) contained in (60). The contact lens after being placed in the contact lens safety apparatus for a period of time can be replaced back into the eye.

6 Claims, 2 Drawing Sheets

CONTACT LENS SAFETY APPARATUS

The present invention relates to the environment of contact lenses and their safety specifically using the method of elevation and de-elevation within sealing means and with contact lens solution in place prior to opening providing an extremely safe, easy and cost effective apparatus for the contact lens user.

The human eye is one of the most important senses and it is obvious that we should take care with anything relating to it. Eye conditions come in different forms like: Myopia (also called short sightedness), Hyperopia (also called hypermetropia or long-sightedness), Presbyopia which is the loss of focussing ability of the eyes, Astigmatism in which the cornea at the front of the eye is oval instead of round, and others like Keratoconus, Meibomian Gland Dysfunction and Computer Vision Syndrome to name but a few.

To help overcome the difficulties named above various types of contact lenses are available in the marketplace including Disposable contact lenses, Leave-in (extended wear) contact lenses, Gas permeable contact lenses, Hard and Soft contact lenses. These can then be made to the prescription of the eye wearer. Even a tint can be added and in the field of fashion contact lenses are available in all sort of forms.

In recent years exiting new developments in the practice of contact lenses have included new materials for soft contact lenses that allow more oxygen to the eye, enabling a more comfortable fit with longer wearing times.

Contact lens solutions which can clean, disinfect and store the lenses are always developing with separate or all in one versions available to the wearer. If we just look at all in one solutions, the vast advancements made in developing how they perform means that carrying out any task to keep a contact lens safe should not be a problem.

Different types of contact lens cases and the way they look after a lens is also available to the marketplace and it is in this area that my invention is closest with a heightened awareness to safety and the handling of the contact lens itself with the contact lens wearer in mind which will compliment the other areas recently developed and improved in relation to the contact lens.

Unfortunately, contact lenses will still be potentially able to collect harmful contaminants that may make their use uncomfortable or make their prescription not work perfectly. These contaminants may include the fluid from the eye, small deposits from soaps, cosmetics, airborne dust and other matter.

Therefore the need to be able to remove these contaminants and keep the contact lens comfortable for users will always be present.

This is where various methods have been invented or tried out to over come this problem in the past. Cleaning the lens where it is submersed in various liquids from cleaning agents to disinfectants, mechanical movements, ultrasonic, chemical reactions, rubbing the lens with fingers are just some examples.

Various designs of contact lens containers have also been disclosed involving closing lids, screw tops, pump actions, sponge chemical reactions with some including separate parts and the necessity to use external equipment or top up solutions.

Some examples of disclosed methods are: WO 94/15729 A1 (Pankow), which discloses an apparatus including a reactive surface which has to be in contact with the lens to help in the migration of contaminants. This includes a chemical reaction process compressing the lens between two surfaces and the possible addition of contact lens solutions, which is to complex and not cost effective; EP 0269367 A2 (Sola) which is a contact lens package including a container including non reusable sealing means. This does not have any safe watertight aspects at all once opened; U.S. Pat. No. 3,955,726 A (Reitzel) discloses a contact lens storage locket which would not be cost effective to make and would include the fishing out action of the contact lens from the container within the locket and be very tricky to use; EP 0694017 A (Allergan) discloses the need for a container which might include a sliding action or adhesive to keep it watertight. This would not be all that safe for a contact lens and the container with prefilled solution again involves fishing about for a contact lens with your fingers; EP 0542686 A1 (Ciba-Geigy), EP 0542686 A1, U.S. Pat. No. 3,822,780 A and U.S. Pat. No. 4,328,890 A (Thomas et al) either include detachable parts, rely on external addition of solutions or the need once again to fish about to find lens.

Document EP 0389418 discloses an elevating member 21, a reservoir 15, a sealing means (screw threads) and a lid 11 communicating with a channel (screw threads) on the reservoir however, there is no mention in this document of the elevating member 21 being self-elevating or of the contact lens solution being prevented from escaping prior to the first opening of the apparatus. In each instance where the elevating member is shown a finger is required to provide the force necessary to elevate it.

Document JP 2001046134 discloses a member 4 and a reservoir 6 however, there is no mention of a sealing means on at least one lid communicating with a channel on a reservoir whereby contact lens solution is prevented from escaping prior to the first opening of the apparatus.

Document DE 4415003 shows a member 2, a reservoir 62 and a sealing means 74, 79 & 69 however, there is no mention of the member being self-elevating indeed it can clearly be seen from the figures that the member 2 is elevated by means 4. Furthermore, there is no mention of the sealing means communicating with a channel on the reservoir or of the contact lens solution being prevented from escaping prior to the first opening of the apparatus.

Document U.S. Pat. No. 3,460,552 discloses a member 19, a reservoir 13 and a sealing means 11 however, there is no mention of the member 19 being self-elevating, indeed elevation of this member is activated by a separate spring 59. Furthermore, nothing is mentioned of the sealing means 11 communicating with a channel on the reservoir or of the contact lens solution being prevented from escaping prior to the first opening of the apparatus.

Document U.S. Pat. No. 3,646,672 discloses a member 36, a reservoir and a sealing means 32 on a lid. There is no mention of a self-elevating member as this device utilises the force of a coil spring to elevate the member 36. There is also no mention of a sealing means communicating with a channel on the reservoir or of the contact lens solution being prevented from escaping prior to the first opening of the apparatus.

Document U.S. Pat. No. 4,942,959 discloses a member 30, reservoirs 14 & 16 and a sealing means 56/58 on a lid communicating with a channel on the reservoir however, there is no mention of the member being self-elevating as it is clearly shown that the member 30 is elevated by its interaction with the fluid 38 furthermore, there is no mention of the contact lens solution being prevented from escaping prior to the first opening of the apparatus.

Document DE 10053798 discloses a member 24 and a reservoir 30 however, there is no mention of a sealing means communicating with a channel on the reservoir or of the contact lens solution being prevented from escaping prior to the first opening of the apparatus.

Document WO 98/15243 discloses a member 18 however, there is no mention of this member being self-elevating, indeed a finger is required to provide the force necessary to elevate it. Furthermore, there is no mention of a sealing means communicating with a channel on the reservoir or of the contact lens solution being prevented from escaping prior to the first opening of the apparatus.

The present invention is directed to the field of contact lens storage devices which only make use of a single solution rather than combinations of chemicals and focuses on the problem encountered by contact lens users, having forgotten their lens cases and/or their solution, that being that they, having set off on a journey for example, find that they need to temporarily remove their lenses but have not got a safe and hygienic place to store their lenses. In this situation a contact lens user would simply use the apparatus according to the present invention rather than using expensive and bulky lens cases, containers of solution and perhaps catalysts. Featured within the invention is the integral lids and the contact lens solution partially filled under a seal and again sealed in the main apparatus. This is to provide security and safety.

Not one of the cited documents are directed to solving this particular problem and therefore may not be used in assessing the obviousness of the present invention. None of the above methods above provide an acceptable safe, cost effective, easy to use and simple hygienic answer to the storing of a contact lens. Moreover the continuous use of fingers and detachable parts do not help make the process of looking after the contact lens very acceptable and the potential high cost of manufacturing can be an issue.

There is therefore still demand for a method to clean, keep moist and hygienically safe a contact lens whilst out of the eye for a period of time which does not have to rely on loose parts, fancy gadgets, increased reliance on fingers which just make the process more difficult to carry out. For example in aeroplanes, trains, first aid kits, places with lack of space to name but a few.

It is an objective of the present invention to obviate or mitigate one or more of the problems associated with the prior art.

Therefore it is my intention to invent a safety contact lens apparatus very cheaply and easily however being compact and safe addressing the issues above.

The advantages of the invention are mainly its overall safety and to decrease the use of finger contact with the lens and decrease the intricate manoeuvres normally associated with the removal and insertion of contact lenses and at the same time keeping the contact lenses stored hygienically safe in a small compact unit which does not have parts that are detachable affecting the safety of the apparatus.

It should be noted that this invention is not to replace the need for contact lens cases or solutions or even contact lenses themselves. This invention is a stand alone method geared towards the safety of the contact lens user when they have forgotten their spare lenses, case or solution. It is also intended to be used where space and safety are a priority. This could be on an Aircraft or Ship to name only two examples out of many.

The invention will now be described with reference to the accompanying drawings in which this is a preferred embodiment.

BRIEF DESCRIPTION OF THE DRAWINGS

FIG. 1 shows the contact lens safety apparatus 1 in an open aspect, prepared to receive at least one contact lens. It can be seen that the apparatus 1 is comprised of a resilient member 5 and a plurality of receiving members 10.

Figure 1:
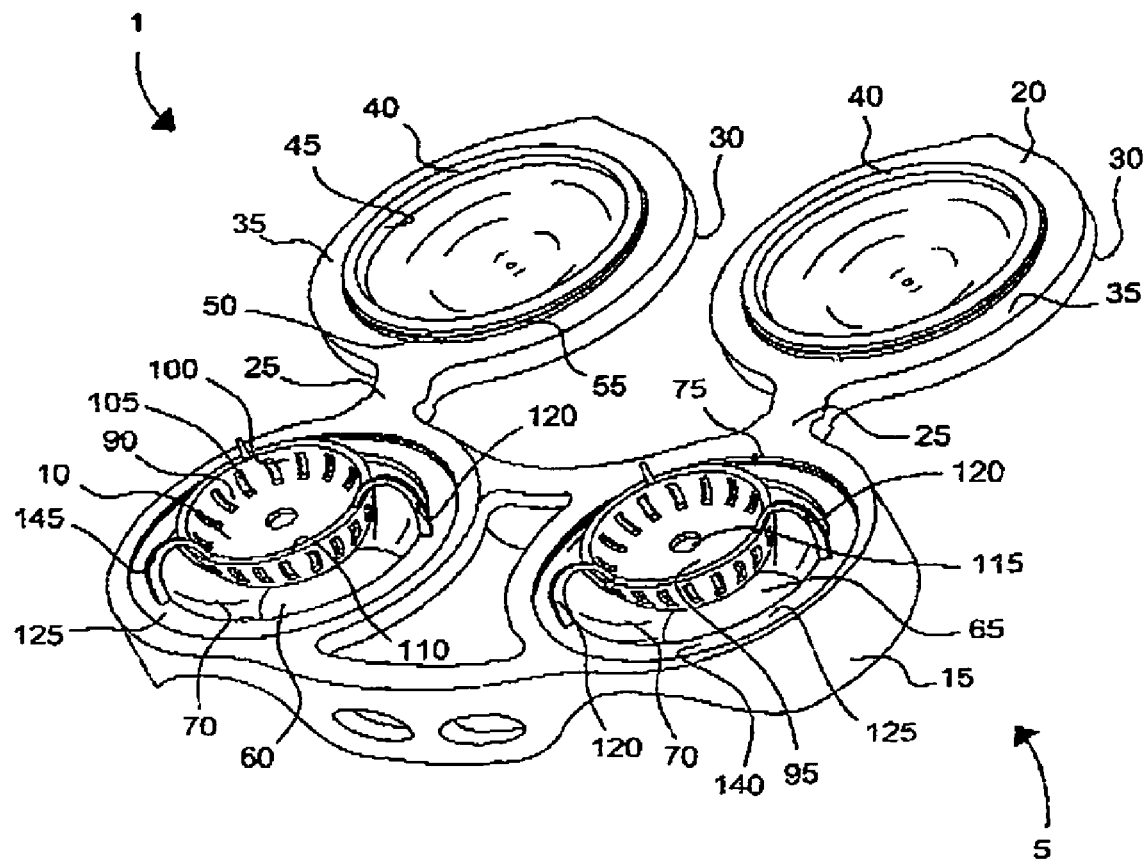
FIG. 1 is a perspective view of the contact lens safety apparatus in accordance with the present invention.

The resilient member 5 has a framing section 15 and a plurality of lids 20 which are substantially circular in form and are hingedly attached to the framing section 15. In the preferred embodiment shown in FIG. 1 the hinging nature of the attachment is achieved by providing an area 25 of reduced thickness between the framing section 15 and the lids 20.

The lids 20 have an outside face 30 and an inside face 35. The inside face 35 of the lids 20 include an annular section 40 coaxial with the lids 20 and protruding from the inside face 35. The annular section 40 having an inner diameter 45 and, an outer diameter 50 that is circumscribed by a sealing means 55, which extends from the outer diameter 50.

The framing section 15 includes a plurality of reservoirs 60 having a bed 65, scalloped sides 70 and a top edge 75. The top edge 75 of the reservoirs 60 is substantially circular. The scalloped sides 70 include a first channel 80 and a second channel 85 (shown in FIGS. 2 & 3). The first and second channels extend around the perimeter defined by the scalloped sides 70 to form two independent unbroken channels and are sited proximal to top edge 75. First channel 80 being sited most proximal to the top edge 75 in order to receive the sealing means 55 when the lids 20 are closed.

The receiving member 10 defines a substantially circular bowl 90 having dimensions suitable for accommodating a contact lens. Bowl 90 includes a base 95 and a substantially circular wall 100, which extends away from the base 95. The wall 100 is similarly shaped to the scalloped sides 70 of the reservoirs 60 and include, around its circumference a plurality of elongate slots 105 extending from a site proximal to the base 95 towards a site proximal a rim 110 of the bowl 90. The bowl 90 further includes an orifice 115 in its base 95 coaxial with the bowl 90. A plurality of resilient means 120 are provided equidistant around the rim 110 of the bowl 90. The resilient means 120 take the form of an inverted U and are connected to each other via an annulus 125, the annulus having an inside 130 and an outside 135. The outside 135 of the annulus 125 being configured to be accommodated by the second channel 85 thereby securely holding the receiving member 10 in position within the reservoir 60. It can be seen from the figures that the annulus 125 has a top surface 140 on which one leg 145 of the resilient means 120 is fixed. It will be noted that the leg 145 of the resilient means 120 does not extend over the full width of the annulus 125 but stops short of the scalloped sides 70 of the reservoir 60. It is to be understood that the reservoir 60 will be partially filled with contact lens solution 150 prior to the first opening of the contact lens safety apparatus 1 however, this solution 150 has not been shown in FIG. 1 to aid clarity.

In use, when a user wants to safely store their contact lens(s) in the contact lens safety apparatus 1 for a period of time the lid(s) 20 are moved from a closed position, (shown in figure three with the lid removed for clarity) to the open position as shown in FIG. 1 by hingedly rotating them about the area 25. As can be seen from FIG. 3, prior to opening the contact lens safety apparatus 1, the resilient means 120 is in an elastically bent position thereby holding the receiving member 10 submerged in the solution 150.

Figure 2:
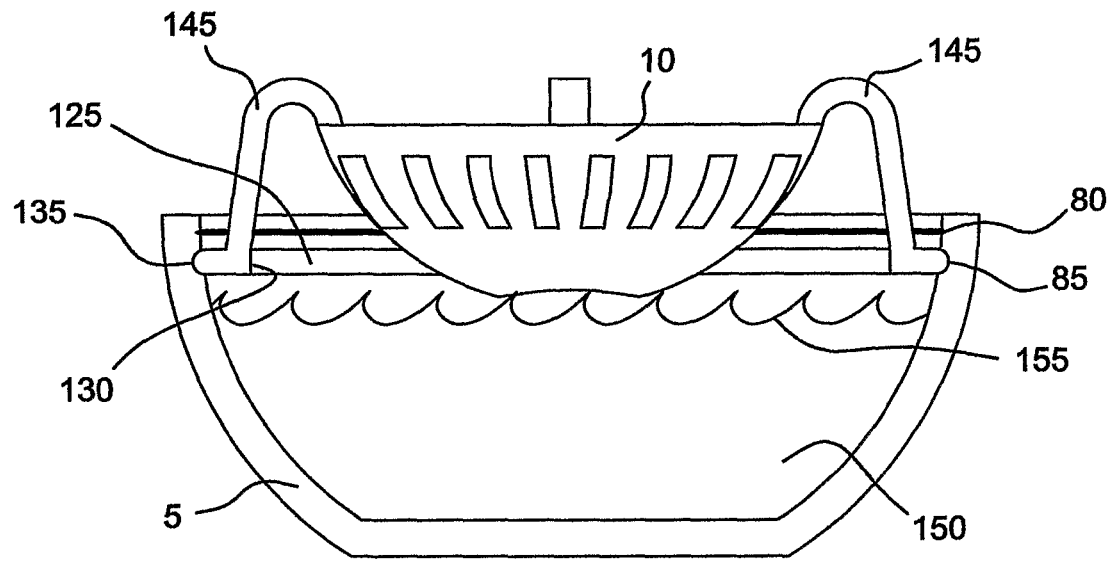
FIG. 2 is a cross-sectional partial view of the contact lens safety apparatus in an open aspect.
Figure 3:
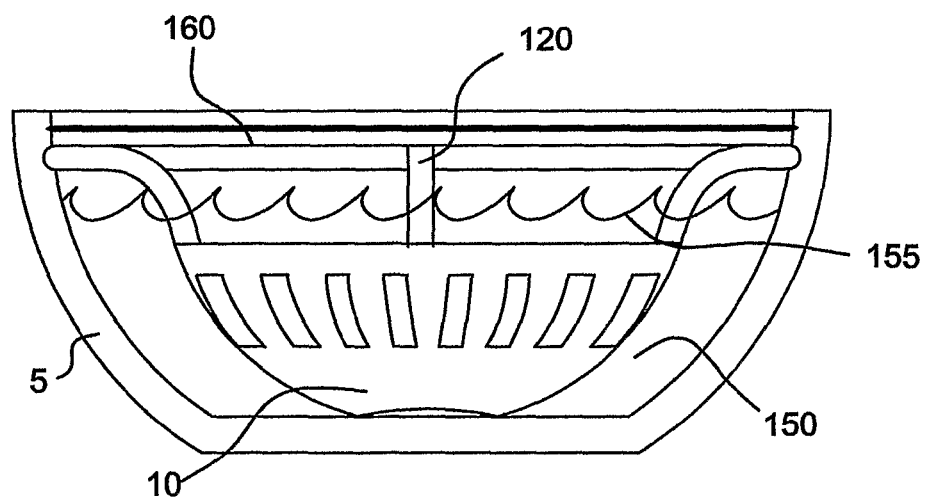
FIG. 3 is a cross-sectional partial view of the contact lens safety apparatus in a closed aspect.

Sealing means 160 is in place on 125 as can be seen in FIG. 3. The sealing means 160 could be of a foil material and could be able to hermetically seal and could be peeled. Upon moving the lids 20 to the open position then removing sealing means 160 the resilient means 120 elastically deforms to return to its relaxed state as can be seen in FIG. 2. This relaxing of the resilient means 120 elevates the receiving member 10 to a point above the solution's surface 155 where the user may place a contact lens safely into the substantially circular bowl 90 of the receiving member 10. When the user has placed their contact lens(s) safely into the bowl 90 they may then move the lids 20 to a dosed position, in doing so the lids 20 initially contact the inverted U shape of the resilient means 120. Upon further dosing of the lids 20 the resilient means 120 undergoes elastic deformation, stressing it and causing the receiving member 10 to become submerged under the solution's surface 155. In moving from a point above the solution's surface 155 to a point under the solution's surface 155 the orifice 115 in the base 95 of the bowl 90 is flooded with the solution 150. Solution 150 also floods through the plurality of elongate slots 105 causing any contaminants or debris on the contact lens to be washed off and to sink to the bed 65 of the Bowl 90.

When the receiving member 10 and contact lens are submerged the lids are further pressed into the closed position thereby engaging the sealing means 55 with the first channel 80 to maintain a releasable seal around the perimeter defined by the scalloped sides 70.

The resilient means 120 having a elastically deformable nature could also be at least in the form of a spring.

With regards to materials, maximum resistance between the contact lens safety apparatus and contact lens and solution will preferably occur. The material could also be able to illuminate to aid in its safety in the dark. Having the material partially transparent could also be an advantage to see contents are present, especially if the lens was tinted or cosmetic.

It should be noted that the self-elevating member could function without the contact lens present.

What is claimed is:

1. A contact lens safety apparatus comprising: at least one self-elevating member wherein the self-elevating member is operable to self-elevate by resilient means wherein the resilient means is a spring, at least one reservoir partially filled with contact lens solution, the reservoir housing the self-elevating member, a first sealing means whereby the solution is prevented from escaping prior to the first opening of the apparatus wherein the first sealing means is of a foil material and is operable to hermetically seal and is arranged to be peeled and a second sealing means on at least one integral lid, wherein the second sealing means is arranged to be received in a channel on the reservoir whereby the contact lens solution is prevented from escaping after the first use of the apparatus.

2. A contact lens safety apparatus as recited in claim 1, wherein the resilient means is an elastically deformable leg.

3. A contact lens safety apparatus as recited in claim 1, further comprising bowls with elongated slots.

4. A contact lens safety apparatus as recited in claim 1, wherein the apparatus is operable to accommodate at least one contact lens and is operable to self-elevate with or without contact lens solution present.

5. A contact lens safety apparatus as recited in claim 1, further comprising materials that Illuminate and which are partially transparent.

6. A contact lens safety apparatus as recited in claim 1, wherein the self-elevating member is integral.

* * * * *